US009409939B2

(12) United States Patent
Wang et al.

(10) Patent No.: US 9,409,939 B2
(45) Date of Patent: Aug. 9, 2016

(54) QUANTIFICATION METHOD FOR REMAINING LIVER FUNCTION AND NOVEL LIVER RECEPTOR IMAGING AGENT

(71) Applicant: INSTITUTE OF NUCLEAR ENERGY RESEARCH ATOMIC ENERGY COUNCIL, EXECUTIVE YUAN, Taoyuan County (TW)

(72) Inventors: Mei-Hui Wang, Taoyuan County (TW); Wuu-Jyh Lin, Taoyuan County (TW); Chuan-Yi Chien, Taoyuan County (TW); Hung-Man Yu, Taoyuan County (TW); Reiko Takasaka Lee, Baltimore, MD (US); Yuan-Chuan Lee, Baltimore, MD (US)

(73) Assignee: INSTITUTE OF NUCLEAR ENERGY RESEARCH ATOMIC ENERGY COUNCIL, EXECUTIVE YUAN, Taoyuan (TW)

( * ) Notice: Subject to any disclaimer, the term of this patent is extended or adjusted under 35 U.S.C. 154(b) by 155 days.

(21) Appl. No.: 13/858,213

(22) Filed: Apr. 8, 2013

(65) Prior Publication Data

US 2013/0225798 A1    Aug. 29, 2013

Related U.S. Application Data

(62) Division of application No. 12/779,374, filed on May 13, 2010, now Pat. No. 8,435,491.

(30) Foreign Application Priority Data

Oct. 26, 2009   (TW) ................................ 98136146 A

(51) Int. Cl.
| | | |
|---|---|---|
| *A61K 51/00* | (2006.01) | |
| *A61M 36/14* | (2006.01) | |
| *C07H 15/04* | (2006.01) | |
| *A61K 51/04* | (2006.01) | |

(52) U.S. Cl.
CPC ............ *C07H 15/04* (2013.01); *A61K 51/0491* (2013.01); *A61K 51/0497* (2013.01)

(58) Field of Classification Search
CPC ..... A61K 51/00; A61K 51/08; A61K 51/088; A61K 51/04; A61K 51/0491; A61K 51/0497; C07H 15/04
USPC ............... 424/1.11, 1.65, 1.69, 1.73, 9.1, 9.6; 534/7, 10–16; 514/1, 1.1
See application file for complete search history.

(56) References Cited

U.S. PATENT DOCUMENTS

| | | | | |
|---|---|---|---|---|
| 4,010,251 | A * | 3/1977 | Green ........................ | 424/1.49 |
| 6,350,431 | B1 * | 2/2002 | Snow ................. | A61K 41/0033 |
| | | | | 424/9.6 |
| 8,142,759 | B2 * | 3/2012 | Wang et al. .................. | 424/1.69 |
| 8,435,491 | B2 * | 5/2013 | Wang et al. .................. | 424/1.69 |
| 8,552,163 | B2 * | 10/2013 | Lee et al. ...................... | 536/17.9 |
| 8,961,931 | B2 * | 2/2015 | Duh et al. ..................... | 424/1.89 |
| 9,040,017 | B2 * | 5/2015 | Wang et al. .................. | 424/1.11 |

OTHER PUBLICATIONS

Lee et al, Bioorganic & Medicinal Chemistry, 2011, vol. 19, pp. 2494-2500.*
Ljungberg, et al., "3D Absorbed Dose Calculations Based on SPECT: Evaluation for 111-In/90-Y Therapy using Monte Carlo Simulations.", 2003, pp. 99-107, vol. 18, No. 1, Cancer Biotherapy & Radiopharmaceuticals.
Royal, et al., "Society of Nuclear Medicine Procedure Guideline for Hepatic and Splenic Imaging 3.0", Jul. 20, 2003, pp. 53-57, Society of Nuclear Medicine Procedure Guidelines Manual.
Kwon, et al., "Functional Hepatic Volume Measured by Technetium-99m-Galactosyl-Human Serum Albumin Liver Scintigraphy: Comparison Between Hepatocyte Volume and Liver Volume by Computed Tomography", 2001, pp. 541-546, vol. 96, No. 2, The American Journal of Gastroenterology.
Miederer, et al., "Realizing the potential of the Actinium-225 radionuclide generator in targeted alpha particle therapy applications", 2008, pp. 1371-1382, Advanced Drug Delivery Reviews.
Virgolini, et al., "Decreased hepatic function in patients with hepatoma or liver metastasis monitored by a hepatocyte specific galactosylated radioligand.", 1990, pp. 937-941, Macmillan Press Ltd.
Korf, et al., "Liver X receptors contribute to the protective immune response against Mycobacterium tuberculosis in mice", Jun. 2009, pp. 1826-1837, vol. 119, No. 6, The Journal of Clinical Investigation.
Mahley, et al., "Two Independent Lipoprotein Receptors on Hepatic Membranes of Dog, Swine, and Man", Nov. 1981, pp. 1197-1206, vol. 68, The American Society for Clinical Investigation, Inc.
Yu, et al., "Radiolabeling and MicroSPECT/CT Imaging of a Novel Multivalent Glycopeptide for Asialoglycoprotein Receptor Imaging", Sep. 2009, vol. 22, Annals of Nuclear Medicine and Sciences.
Satoh, et al., "99mTc-GSA liver dynamic SPECT for the preoperative assessment of hepatectomy", 2003, pp. 61-67, vol. 17, No. 1, Annals of Nuclear Medicine.

* cited by examiner

*Primary Examiner* — D L Jones
(74) *Attorney, Agent, or Firm* — WPAT, PC; Justin King

(57) ABSTRACT

A test indicator for quantifying remaining liver function is provided. A novel liver receptor imaging agent with liver targeting property is utilized to develop a method for quantifying remaining liver function to serve as test indicator for judging the liver failure outcome in clinic, particularly for judging the necessity of liver transplantation for patients with liver failure or liver disease. The radioactivity uptake of the test indicator was negatively correlated with the extent of liver reserve. The cutoff value of liver reserve for liver transplantation is also disclosed.

1 Claim, 9 Drawing Sheets

QUANTIFICATION METHOD FOR REMAINING LIVER FUNCTION AND NOVEL LIVER RECEPTOR IMAGING AGENT

CROSS REFERENCE TO RELATED PATENT APPLICATION

This application is a divisional application of co-pending U.S. application Ser. No. 12/779,374, filed May 13, 2010, which claims the benefit of Taiwan application Serial No. 098136146, filed on Oct. 26, 2009, the contents of which are incorporated herein by reference.

BACKGROUND OF THE INVENTION

1. Field of the Invention

The present invention relates to a quantification method for remaining liver function, and a novel liver receptor imaging agent with liver targeting property.

2. Related Art

Asialoglycoprotein receptor (ASGPR) in the liver is known to specifically bind to glycopeptides or glycoproteins having Gal or GalNAc on an end. When liver lesion occurs, the number of ASGPR will change, but there is not a systematic quantitative evaluation tool that has been widely accepted. Therefore, it is desirable to develop glycopeptides or glycoproteins with a Gal or GalNAc end to serve as liver receptor imaging agent. The liver receptor imaging agent has the following utilities in the industry.

1. Liver transplantation often fails due to transient hypoxia, and whether the liver transplantation is successful or not can be immediately known through liver receptor imaging after the transplantation.

Liver receptor imaging is indicative of actual liver function. After binding with ASGPR, glycopeptides or glycoproteins with Gal and GalNAc end enter hepatocytes through receptor-mediated endocytosis. When liver lesion occurs, the liver receptor is reduced, and the imaging level will be reduced. Thus, the actual liver function can be evaluated by the imaging level theoretically.

2. Liver receptor imaging can be used to evaluate the anti-hepatitis and anti-fibrotic effects of Chinese herbal medicines.

3. The liver receptor imaging agent has highly specific liver targeting property, and can effectively carry medicines to be accumulated into liver at a concentrated dosage, so that not only the used dosage and treatment cost can be significantly reduced, but also the generation of side effects can be effectively reduced.

4. The liver receptor imaging agent has highly specific liver targeting property and is highly safe, and can be used as gene delivery vector for liver without any unnecessary allergic immune response.

This type of liver receptor imaging agents has the potential of quantifying the liver storage function. Meanwhile, there is an urgent need for an agent to determine the remaining liver function in clinic, to help clinicians to determine whether a liver transplantation is necessary or not for a patient. In Taiwan, there are 3,000,000 patients with hepatitis B, 500,000 patients with hepatitis C, and numerous patients with drug-induced hepatitis, all of whom are at high risk of liver failure, and need regular assessment of liver storage function.

Presently, the peptides or proteins to be polymerized with saccharide groups that have been disclosed in documents and patents include albumin, tyrosine-glutamyl-glutamic acid (YEE), tyrosine-aspartyl-aspartic acid (YDD), and tyrosine-glutamyl-glutamyl-glutamic acid (YEEE).

Tc-99m-Galactosyl-Serum-Albumin (Tc-99m GSA) is known as a liver receptor imaging agent, and has been used in clinic in Japan. But, GSA is a protein, and is a biological product having a very high molecular weight of about 67 kD. Therefore, it is difficult to know the position and the number of the saccharide group and DTPA connected to the protein exactly even with MS. In contrast, YEE, YDD, YEEE are peptides having a molecular weight of 1-2 kD. For them, the position and the number of the saccharide group and DTPA connected to the peptide can be predicted with MS, thus the quality control procedure is significantly simplified compared with GSA.

YEE and YDD are firstly set forth by Lee (1983), and YEEE is an improved invention by Chen (TW1240002, 2000). In 1983, Lee set forth that the binding force between galactosamine peptide with two chains in series and hepatocyte receptor is 1000 times of that of galactosamine peptide with a single chain, and the binding force between galactosamine peptide with three chains in series and hepatocyte receptor is $10^6$ times of that of galactosamine peptide with a single chain. It is necessary to find a scaffold having at least three functional groups to polymerize three galactosamine chains together, for which a polymerized amino acid, i.e., peptide, is useful, for example, glutamyl-glutamic acid (EE, in which glutamic acid is represented as E), aspartyl-aspartic acid (DD, in which aspartic acid is represented as D), and lysine-lysine (KK, in which lysine is represented as K). Both EE and DD have three COOH functional groups being exposed and can thus be jointed with three galactosamine peptides having a certain length. Due to pKa in an acidic range, the product can be precipitated in an acid, thus facilitating separation and purification. As for KK, it has three amino groups and one COOH functional group, with the three amino groups being not easily linked to the saccharide chains, so it has not been used to develop liver receptor imaging agent till now.

In order to facilitate iodine isotope labeling, EE and DD are attached with Y (tyrosine), allowing in vivo imaging or cell receptor binding test. However, for the iodine labeling of YEE or YDD, it is necessary to add an oxidant, such as chloramine T, Iodobead, or Iodogen. In case of in vivo imaging, it is necessary to remove the oxidant by purification at the end of the reaction, because the oxidants are toxic to human body.

SUMMARY OF THE INVENTION

Accordingly, in order to solve the problems, the present invention provides a quantification method for remaining liver function and a novel liver receptor imaging agent. For 740 patients waiting for liver transplantation in Taiwan, by using this method, those patients in urgent need for liver transplantation can be immediately picked out, and meanwhile, for the persons interested in organs donation, suitable individuals for liver donation can be immediately selected out. Thus, the accuracy of the determination of liver transplantation can be enhanced.

Furthermore, in order to avoid the shortcomings of iodine labeling, a new liver targeting drug different from YDD and YEE but suitable for labeling with In-111, Tc-99m, Gd and Ga-68 is provided. The radioelements or metal for MRI, such as, In-111, Tc-99m, Ga-68 and Gd, are nuclides well-known to have very low toxicity, and no addition of toxic oxidants, such as, chloramine T, Iodobead, or Iodogen, are needed during the radiolabeling process.

In one aspect, the present invention provides a method for quantifying remaining liver function. A liver receptor imaging agent is intravenously injected as agent, and then the radioactivity per square unit in liver is quantified by SPECT/CT image quantitative analysis, so as to determine the remaining liver percentage at which an individual cannot survive in clinic.

In another aspect, the present invention provides a novel liver receptor imaging agent with liver targeting property. A derivative of a single amino acid is used as backbone for polymerizing with saccharide groups, and the α-amino group on lysine is subjected to reductive alkylation with glycolic acid, such that the N atom carries 2 $CH_2COOH$ groups, which, together with a COOH group of lysine itself, can be polymerized with 3 saccharide groups. Meanwhile, due to a free amino group itself, lysine can be attached with a radioisotope or metal, such as In-111, Tc-99m, Ga-68 and Gd through the bridging of diethylene triamine pentaacetate (DTPA) or 1,4,7,10-tetraazacyclododecane-N,N',N,N'-tetraacetic acid (DOTA), to serve as a novel liver targeting nuclear medicine. Compared with iodine labeling, no oxidant is used, and the toxicity is very low. In view of the binding force with liver receptor, in the present invention inexpensive lactose is used instead of expensive galactose, and in use, two three-chain lactoside molecules are connected together in series with glutamic acid or aspartic acid. The binding force of lactose to the liver receptor is not as high as that of galactose, but after two three-chain lactoside molecules are connected together in series via glutamic acid or aspartic acid, the binding force with liver receptor can also reach the same level as that of YEE and YDD, thus improving the economic effect. The present invention provides a new liver targeting drug different from YEE and YDD but suitable for labeling with In-111, Ga-68, Gd or Tc-99m.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

The features and implementation of the present invention are described in detail with preferred embodiments below.

I Design of Novel Liver Targeting Drug

Figure 1:
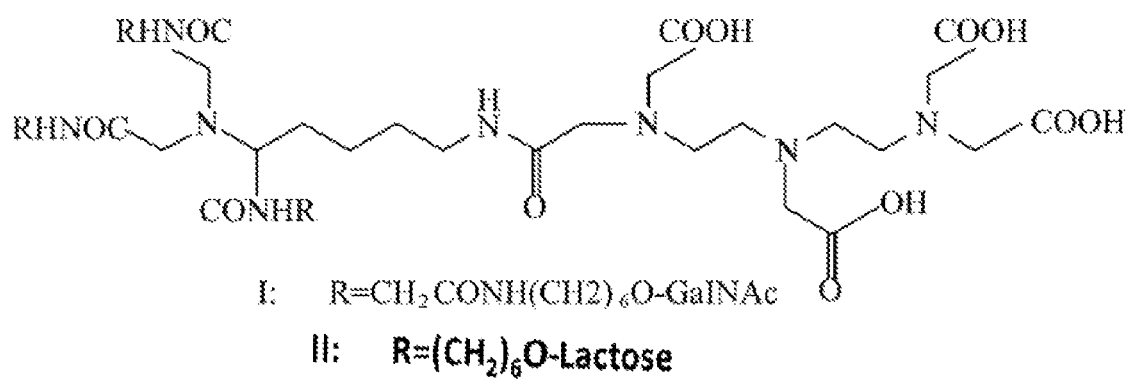
FIG. 1 is a structural representation of the liver targeting drug.
Figure 1:
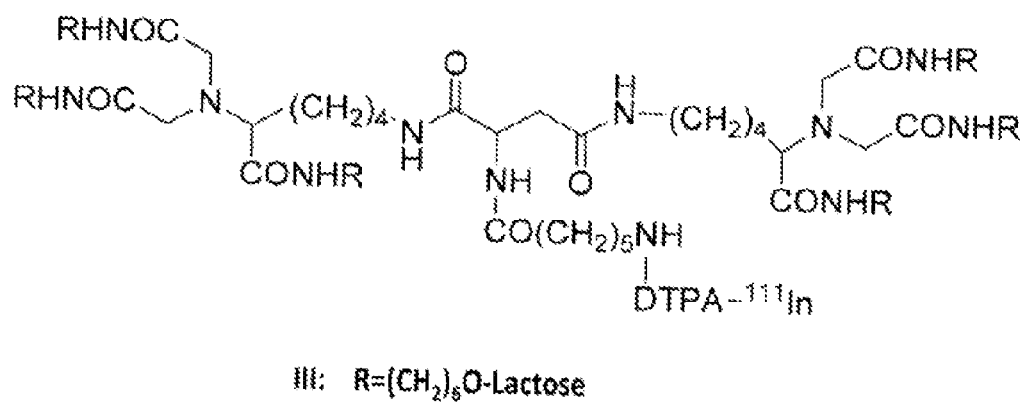

According to the present invention, ε-benzyloxycarbonyl-α-dicarboxylmethyl-L-lysine (Z-DCM-Lys) is used as a new basic structure to be connected to aminohexyl β-GalNAc (ah-GalNAc), glycyl-aminohexyl β-GalNAc (Gah-GalNAc), or aminohexyl Lac (ah-Lac) in series, so as to form a three-chain glycopeptide. As the binding strength of the lactose chain and the ASGPR is not as strong as that of the galactosamine chain, when the lactose chain is connected in series, two molecules of three-chain lactoside will be further connected together in series through aspartic acid or glutamic acid. For example, two molecules of ε-Z-α-DCM-Lys (ah-Lac)$_3$ is further connected together through aminohexanoyl aspartic acid (AHA-Asp) in series to form AHA-Asp[DCM-Lys(ah-Lac)$_3$]$_2$ (hereafter simply referred to as hexa-Lactoside). The free amino end of the hexa-Lactoside can react with DTPA anhydride in a sodium carbonate solution to form a DTPA derivative of AHA-Asp[DCM-Lys(ah-Lac)$_3$]$_2$, the structure of which is as shown in FIG. 1.

II Analysis of Binding Strength of Saccharide Chain Peptide and Murine Hepatocyte With Eu-asialo-orosomucoid (Eu-ASOR) as reference material, the binding strength of saccharide chain peptide and murine hepatocyte is determined by comparing whether the binding degree of saccharide chain peptides, such as DCM-Lys(ah-GalNAc)$_3$, DCM-Lys(Gah-GalNAc)$_3$, DCM-Lys(ah-Lac)$_3$, AHA-Asp[DCM-Lys(ah-Lac)$_3$]$_2$ with murine hepatocyte is higher than that of Eu-ASOR or not, in which the binding degree is expressed by $IC_{50}$ (concentration of 50% inhibition), and the lower the $IC_{50}$ is, the higher the binding degree is. The murine hepatocyte (from Lonza Biotechnology Company, Maryland) is plated in a 24-well plate in advance, and the reaction occurs in each well, into which (i) Eu-ASOR 10 nM (ii) hepatocyte basic medium with 5 mM calcium chloride, and (iii) five different concentrations of saccharide chain peptide of 1 uM-0.8 nM are added. After culturing with shaking for 1 hr, the substance that has not been bound to hepatocyte is removed by washing with the hepatocyte basic medium containing calcium chloride.

Time-resolved fluorescence spectroscopy is preformed, that is, an enhancement solution (15 uM β-naphthoyl trifluoroacetone, 50 uM tri-n-octyl-phosphine oxide, 0.1% triton X-100 in 0.1M acetic acid, titrated with potassium hydrogen phthalate to pH 3.2) is added. The enhancement solution reacts with $Eu^{3+}$ to form a Eu chelate, which can emit a light of 615 nm when being excited at 340 nm. With the logarithm of the concentration of saccharide chain peptide as X axis, the emitted fluorescence value as Y axis, the fluorescence value without adding glycopeptide being set as 100%, the $IC_{50}$ of each saccharide chain peptide can be calculated accordingly. It can be known from the data that, the binding of AHA-Asp [DCM-Lys(ah-Lac)$_3$]$_2$ and ASGPR can reach the same binding strength as that of YEE or YDD, but the binding of DCM-Lys(Gah-GalNAc)$_3$ and ASGPR is 10 times of that of YEE or YDD, as shown in Table 1.

TABLE 1

Comparison of binding strength of various saccharide chains and murine hepatocyte

| Compounds | IC50 (nM) |
|---|---|
| YEE(ahGalNAc)$_3$ | 10 nM |
| YDD(GahGalNAc)$_3$ | 10 nM |
| DCM-Lys(ahGalNAc)$_3$ | 10 nM |
| DCM-Lys(GahGalNAc)$_3$ | 1 nM |
| AHA-Asp[DCM-Lys(ahLac)$_3$]$_2$ | 10 nM |

III Method of Radiolabeling Liver Receptor Imaging Agent

Figure 2:
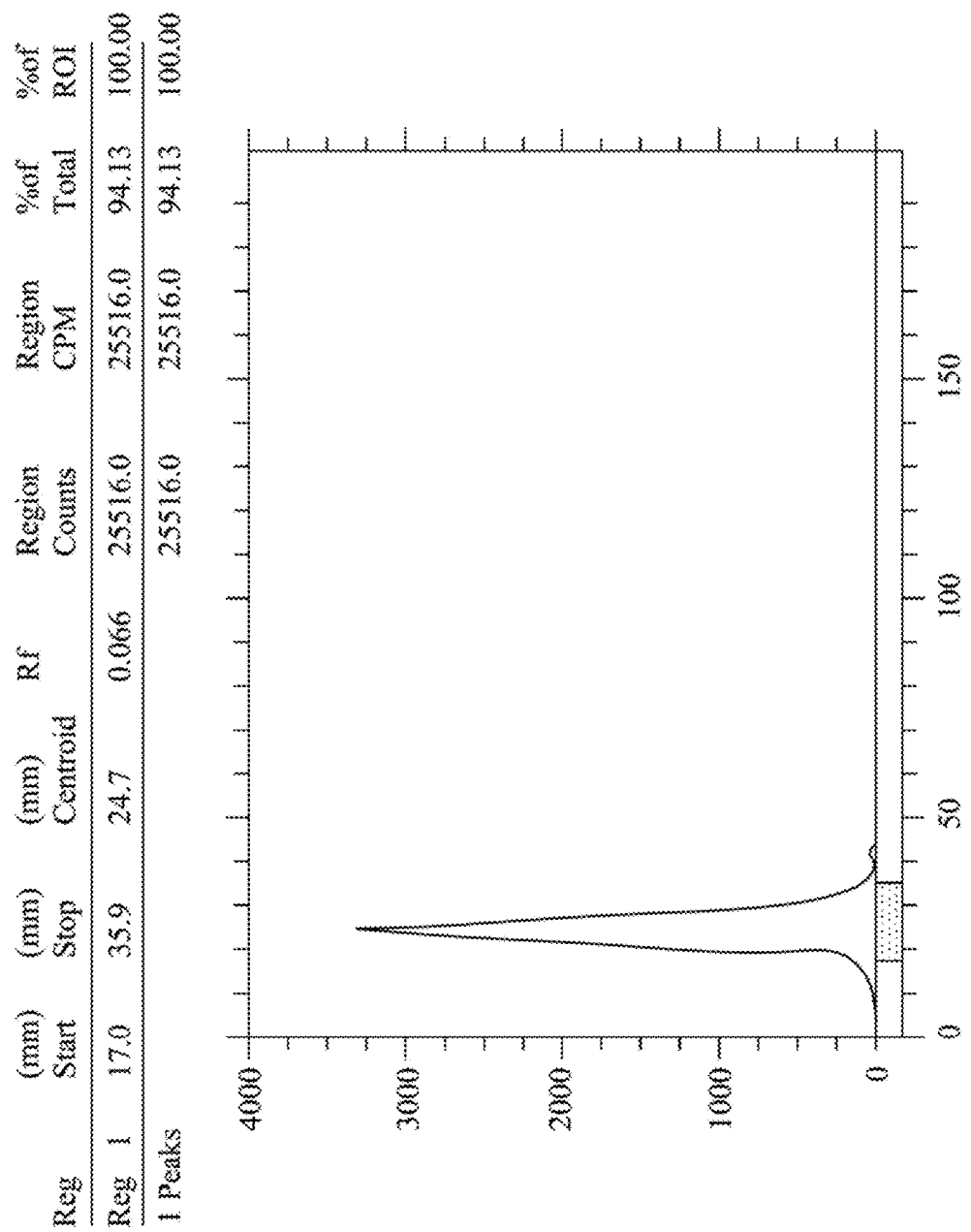
FIG. 2 is a rapid thin-layer chromatography (TLC) spectrum of In-111-DTPA-lactoside, in which the radiochemical purity is up to 99%, and the specific radioactivity is $2.5 \times 10^{10}$ Bq/mg.

30 µCi In-111 ($6\times10^{-13}$ moles) is reacted with 43.8 ng DTPA-hexa-lactoside glycopeptide ($1.2\times10^{-11}$ moles) in 0.1M citric acid, pH 2.1 for 15 min, and the radiochemical purity of In-111-DTPA-lactoside is determined by radio-ITLC (instant thin-layer chromatography. Briefly, a sample of the reaction product above is spotted on an ITLC-SG strip, and is placed in a developing chamber with 10 mM citrate buffer (pH 4) for development. When the liquid level reaches the development end point, the strip is taken out, and placed in a fume chamber for drying, and then scanned with a radio-TLC analyzer, to analyze Rf value (retention factor, which is distance traveled by the analyte divided by distance traveled by the mobile phase). In-111-hexa-lactoside will stay around its origin, and free In-111 and In-111 DTPA will stay at the front of the developing phase. Individual spectrum is plotted and integrated. As a result, the radiochemical purity is up to 99%, and the specific radioactivity is $2.5\times10^{10}$ Bq/mg, as shown in FIG. 2.

IV Bio-Distribution

Figure 3:
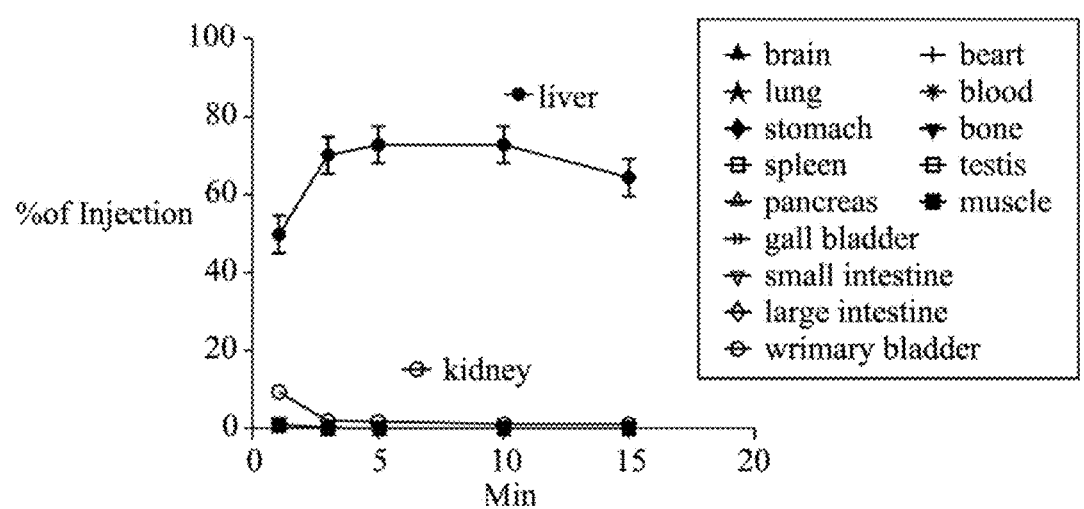
FIG. 3 is a pharmacokinetic distribution data graph of In-111 hexa-lactoside in an organism (mouse)

In-111 hexa-lactoside (200 nCi/g) is injected via tail vein into mice, and the mice are sacrificed at 1 min, 3 min, 5 min, 10 min, 15 min, 1 hr, 24 hr by cervical dislocation, and organs in body are taken out to collect biological samples of mice, including whole blood, brain, muscle (thigh), bone, stomach, spleen, pancreas, small intestine, large intestine, lung, heart, kidney, gallbladder, liver, bladder, urine, etc. The samples are weighed and then placed in a measuring tube. The organs and the standards are placed in a Gamma counter (Cobra II Auto-Gamma Counter, PACKARD, U.S.A) for measurement, to calculate the percentage of injected dose per organ (% ID). The experimental data is presented as mean±standard error of mean (mean±SEM), and time-activity curve is plotted, thereby the actual radiation dose distribution in the body is calculated. As shown in FIG. 3, nearly 80% of the activity is accumulated in liver, and no absorption is in other organs except urine. As 75% of the blood flow of mice is concentrated in the kidney, part of the radioactivity is inevitably distributed in the urine. If the distribution in urine is ignored, the distribution in liver is nearly 100%, which is sufficient to prove the liver targeting characteristics.

V Whole-Body Autoradiography

Figure 4:
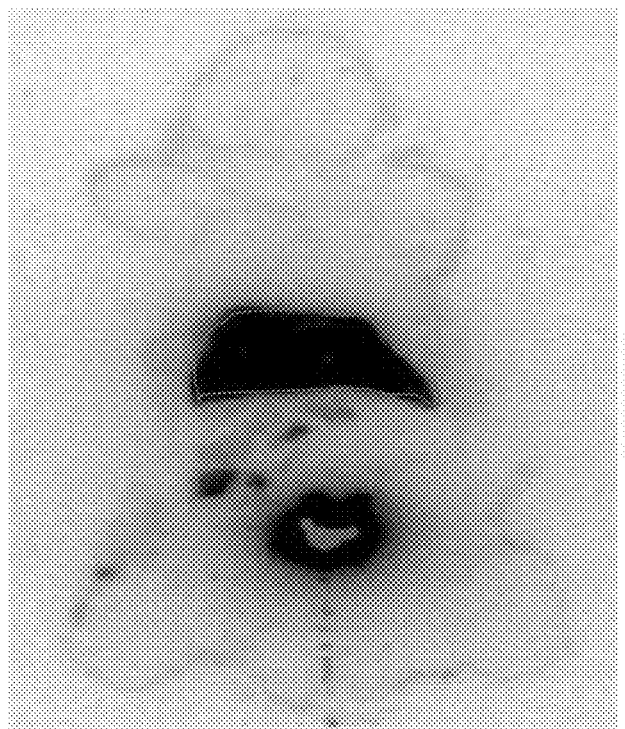
FIG. 4 is a whole-body autoradiography image of an organism (mouse)

In-111 hexa-lactoside (200 nCi/g) is injected via tail vein into mice, and after 15 min of distribution, whole-body freezing microtomy is performed (CM 3600, Leica Instrument, Germany) to obtain sections of 20-30 µm in thickness. The radioactivity is exposed onto X-ray films. A selected section is placed on an IP plate and then placed into a cassette, and exposed with X-ray films at −20☐, thus the radioactivity on the organ will be imaged on the corresponding position on the X-ray film, and the image intensity is in proportion to the radioactivity intensity on the organ (autoradiography). The image is analyzed with BAS-1000, Fuji Film Image reader, and Image Gauge software, to get whole-body autoradiography image, as shown in FIG. 4. The autoradiography image is consistent with the bio-distribution data, that is, radioactivity is merely present in liver and urine.

Figure 5:
FIG. 5 is a SPECT/CT tomography image by liver receptor imaging agent.
Figure 12:
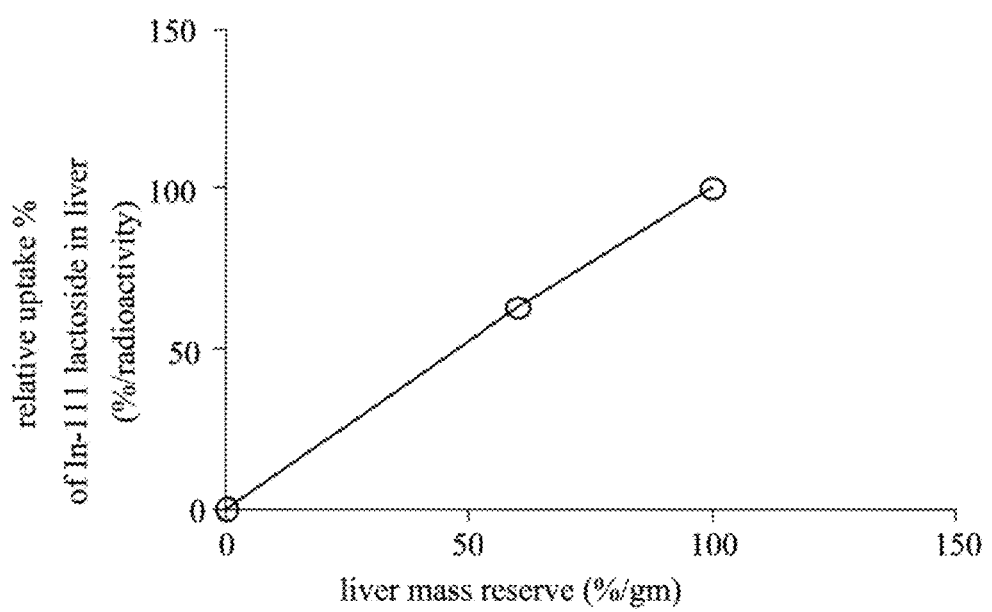
FIG. 12 shows the correlation of liver mass reserve and relative uptake % of In-111 hexa-lactoside in liver.

VI SPECT/CT Image Quantitative Analysis and Tomography by Liver Receptor Imaging Agent In-111 hexa-lactoside (200 nCi/g) is injected via tail vein into mice, SPECT/CT (Gamma Medica Idea (GMI) X-SPECT) is performed immediately after injection, and the imaging lasts for 15 min with a medium energy parallel-hole collimator. In imaging, the animals for experiment are anaesthetized by isoflurane, and after imaging, the SPECT/CT image fusion is preformed, as shown in FIG. 5. The SPECT/CT image is consistent with the bio-distribution and autoradiography image data, that is, radioactivity is merely present in liver and urine. Therefore, the position of liver is selected to quantify the image intensity in the liver. The radioactivity per square mm of liver was measured and analyzed by the SPECT medical imaging instrument. The radioactivity absorbed by liver in a normal group was set as 100% of remaining liver function. Then we could determine the relative remaining liver function by comparing the radioactivity absorbed by liver in each disease group with that in normal group. To verify the accuracy of this imaging method for determination of remaining liver function, we performed 40% hepatectomy and measured In-111 hexa-lactoside uptake. The results are shown in FIG. 12. In the 40% hepatectomized mice, the remaining liver function measured by this In-111 hexa-lactoside imaging method was 63%, in consistence with 60% liver mass remained after hepatectomy. The liver reserve measurements on 40% hepatectomized mice support the accuracy of the In-111 hexa-lactoside imaging agent being a good indicator of remaining liver function.

VII Establishment of Animal Model of Acute Hepatitis and Liver Failure and Measurement of Remaining Liver Function A dose of 250 mg/kg and 500 mg/kg of acetaminophen is each injected into 6-week old Balb/c mice (weighed about 20 g) intraperitoneally, and whether the mice are dead or not is observed within one week. When sacrificing, blood is collected for measuring AST, ALT, bilirubin, and albumin of the serum, and the liver tissue is collected and cut into pathological slices. The liver cell death is observed, and the death rate is estimated. The dose causing a half of mice dead is taken as the dose of the drug inducing liver failure.

Figure 6:
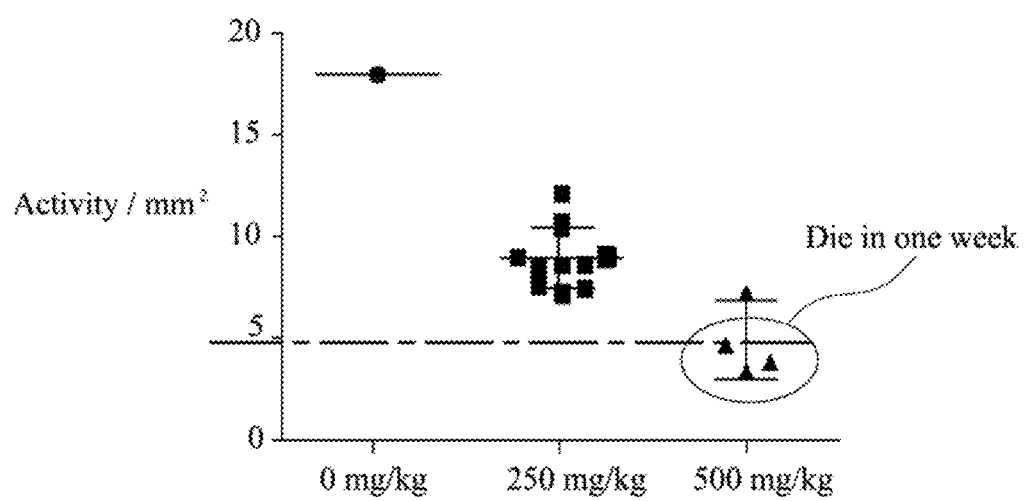
FIG. 6 shows the measurement of liver radioactivity for SPECT/CT image in a series concentration of acetaminophen-treated mice.

After intraperitoneal injection of acetaminophen into the mice, acute hepatitis is induced, and at this time, In-111 hexa-Lactoside (200 nCi/g) is injected via tail vein into the mice with acetaminophen-induced acute hepatitis. SPECT/CT image quantitative analysis and tomography are performed, and the position of liver is selected to measure the image intensity. The liver radioactivity after SPECT/CT imaging in the acute hepatitis group and the normal group is measured, and the results show that after acute hepatitis is induced by acetaminophen, the absorption of In-111 hexa-Lactoside in liver is lower than that of the normal group, and the higher the dose of acetaminophen for inducing is, the lower the radioactivity absorbed in liver is. Further, when the radioactivity absorbed in liver is lower than a certain value, the mice will die within a week. As for mouse, when the remaining liver function is merely 25% of that of the normal group, the individual will die without liver transplantation. The results are shown in FIG. 6.

VIII Establishment of Animal Model of Bile Duct Ligation-Induced Chronic Hepatitis and Measurement of Remaining Liver Function The SD rats are subjected to bile duct ligation, and sacrificed after six to eight weeks. The bloods are collected for biochemical assay, and tissues are collected and cut into pathological slices for histocytochemical stain, to confirm liver fibrosis or cirrhosis.

Figure 7:
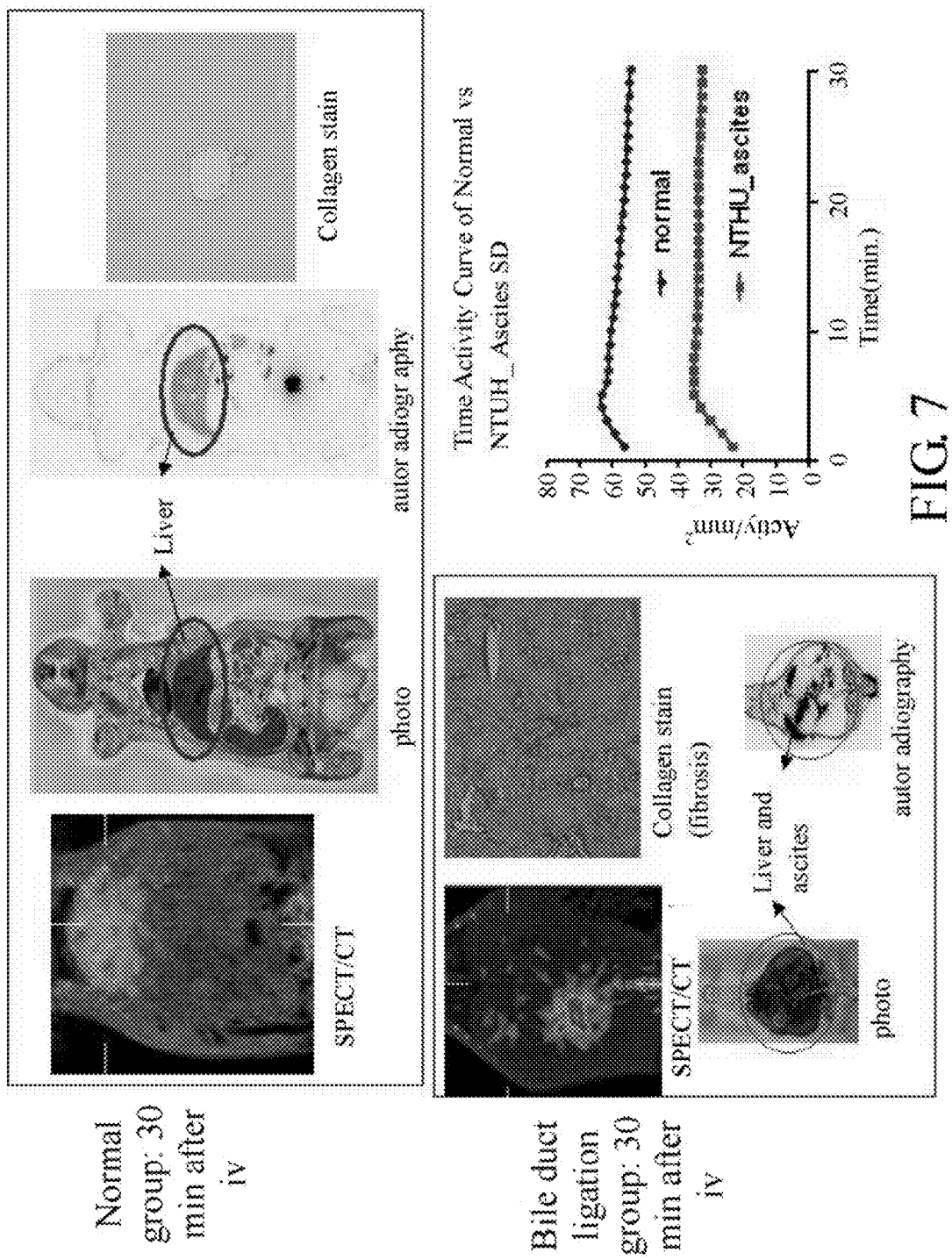
FIG. 7 shows the measurement of the liver radioactivity in a bile duct ligation-induced chronic hepatitis group and a normal group after SPECT/CT imaging.

It approximately costs 4 months for SD rats to generate liver fibrosis induced by bile duct ligation with the generation of ascites. At this time, In-111 hexa-Lactoside (200 nCi/g) is injected via tail vein into the SD rats with bile duct ligation-induced chronic hepatitis. The SPECT/CT image quantitative analysis and tomography are performed, and the position of liver is selected to measure the image intensity. The results show that the absorption of In-111 hexa-Lactoside in liver of the bile duct ligation-induced chronic hepatitis group is lower than that of the normal group, as shown in FIG. 7.

IX Establishment of Animal Model of Thioacetamide-Induced Liver Fibrosis and Measurement of Remaining Liver Function In the experiment, 4-5-week old Balb/c mice are used. 0.03% thioacetamide is added in the drinking water of the mice. After two weeks of drinking, if the weight of the mice is stable, then the concentration of thioacetamide is increased to 0.04%. The drinking water is changed every 2-3 days, and mice are fed for 10 weeks. The mice are weighed every week and the weights are recorded. In order to get different severity, in the uniform experiment group, some of mice are subjected to the experiment after 10-week drinking immediately, and some are subjected to the experiment after 14-16 week feeding.

Figure 8:
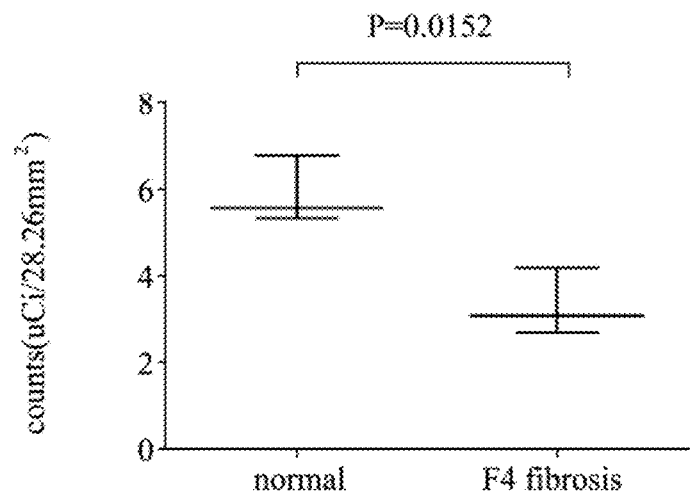
FIG. 8 shows the measurement of the liver radioactivity in a thioacetamide-induced liver fibrosis group and a normal group after SPECT/CT imaging.
Figure 9:
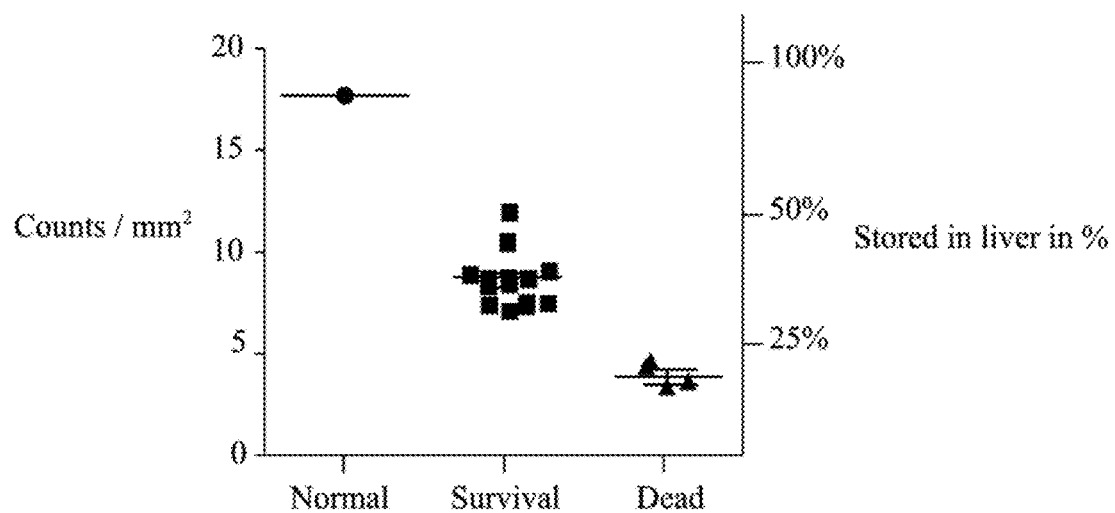
FIG. 9 shows the measurement of liver radioactivity for SPECT/CT imaging in groups of normal, dead and survival from acetaminophen-treated mice.

It approximately costs 2 months for mice to generate thioacetamide-induced liver fibrosis, and at this time, In-111 hexa-Lactoside (200 nCi/g) is injected via tail vein into the mice with thioacetamide-induced liver fibrosis. The SPECT/CT image quantitative analysis and tomography are performed, and the position of the liver is selected to measure the image intensity. The liver radioactivity after SPECT/CT imaging in the thioacetamide-induced liver fibrosis group and the normal group is measured, and the results show that the absorption of In-111 hexa-Lactoside in liver of the mice of the thioacetamide-induced liver fibrosis group is significantly lower than that of the normal group, as shown in FIG. 8. It indeed there is significant difference in the radioactivity uptake between normal mice and F4 fibrosis (p=0.0152 based on two tailed t test).

X Assay of Pathological Tissue Slices and Clinical Biochemical Assay

The liver tissue is collected and cut into slices having a thickness of about 5-7 μm, which is dyed with hematoxylin & eosin stain and observed with microscope for taking photos. The liver fiber tissue (diagnosis of liver fibrosis and cirrhosis) is dyed with Sirius red to know the severity of fibrosis/cirrhosis, as shown by the collagen stains in FIGS. 7 and 8. In clinic, the blood biochemical assay is to measure the liver-related biochemical indicators, such as, AST, ALT, bilirubin, and albumin with an automatic machine.

XI Cell Toxicity Test

Figure 10:
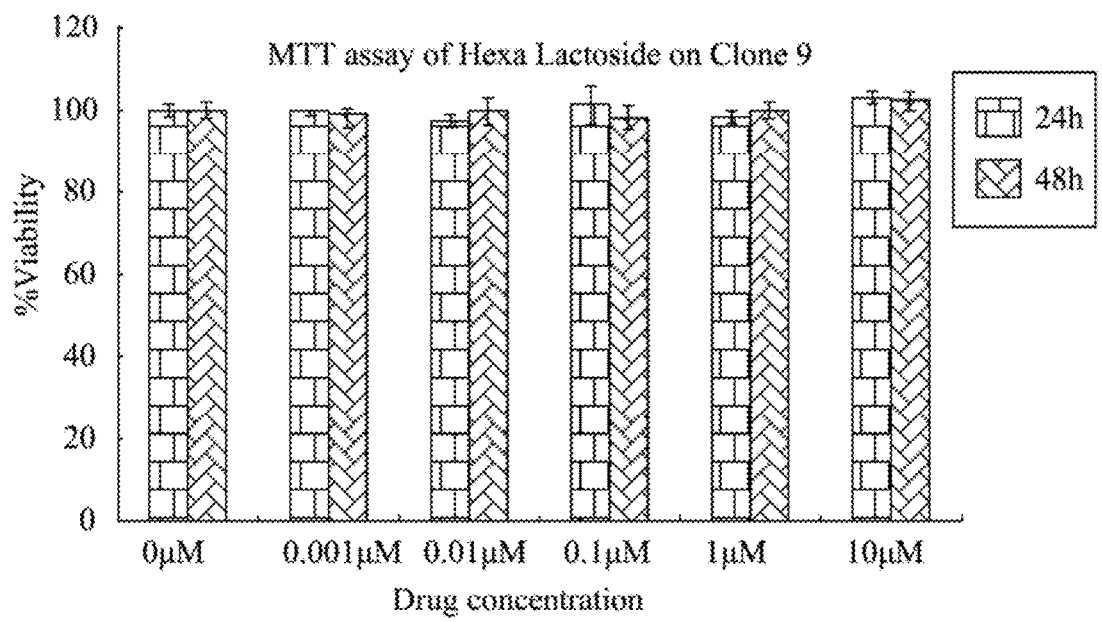
FIG. 10 is a comparison of cell viability of hexa-lactoside in normal rat cell (Clone 9)
Figure 11:
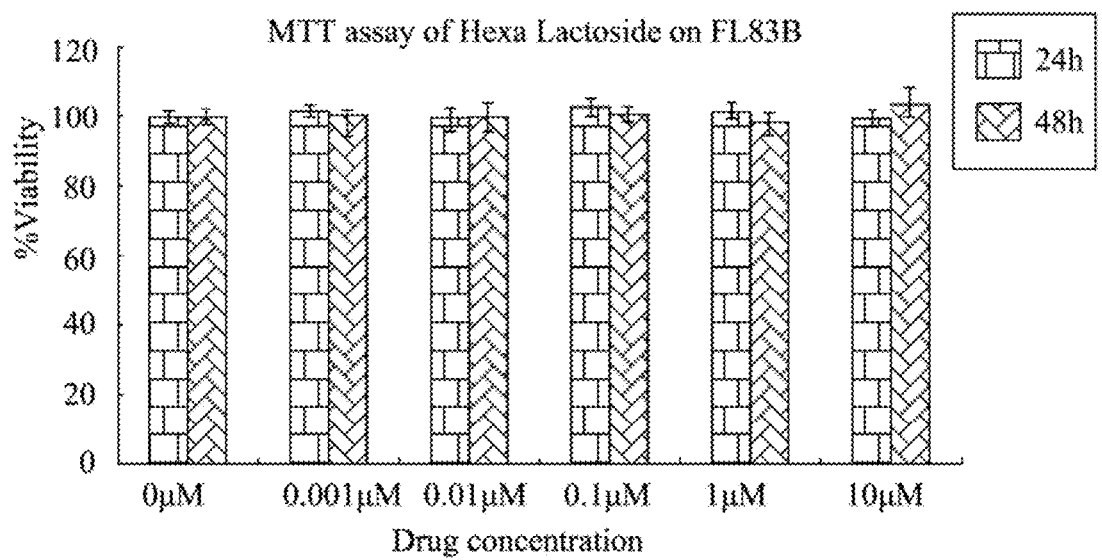
FIG. 11 is a comparison of cell viability of hexa-lactoside in normal mouse cell (FL83B).

MTT, i.e. 3-(4,5-cimethyl-thiazol-2-yl)-2,5-diphenyl tetrazolium bromide, can be metabolized by succinate dehydrogenase of cell mitochondria into blue MTT formazan, and thus is widely used to detect cell viability. The experimental method includes: adding 0, 0.001 μM, 0.01 μM, 0.1 μM, 1 μM, and 10 μM hexa-lactoside into $1\times10^6$ normal rat cells (Clone 9) and normal mouse cells (FL83B), respectively; after culturing for 24 hr, 48 hr, adding MTT; and 4 hr later, dissolving the cells with DMSO. The blue MTT formazan is soluble in the solution. The absorption of the solution at 570 nm is detected. With the absorption at 570 nm without adding hexa-lactoside as 100% of cell viability, the experimental groups with hexa-lactoside added are compared with the normal group without adding hexa-lactoside, to get the cell viability of the experimental groups. The results are shown in FIGS. 10 and 11. FIG. 10 is a comparison of cell viability of hexa-lactoside in normal rat cell (Clone 9), and FIG. 11 is a comparison of cell viability of hexa-lactoside in normal mouse cell (FL83B), in which the concentration used presently is 0.01 μM. The two figures both show that, even when the concentration of hexa-lactoside is $10^3$ times of the concentration, the cell viability is still maintained at 100%, which indicates that the drug hexa-lactoside is safe.

Although the specific embodiments have been illustrated and described above, it will be apparent to those skilled in the art that various modifications and variations can be made in the present invention without departing from the scope or spirit of the invention. Furthermore, the present invention is not limited to the particular forms, and covers all modifications and variations of this invention provided they fall within the scope of the following claims and their equivalents.

In view of the above, in terms of its general combination and features, the present invention has no been found in similar products, and has not been disclosed before its filing date. It indeed meets the requirements of a patent and we thus propose this application according to the provisions of the patent law.

What is claimed is:

1. A liver receptor imaging agent, with the chemical formula:

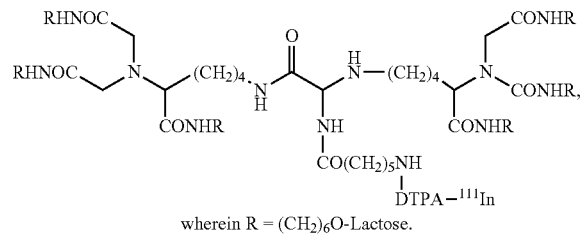

wherein $R = (CH_2)_6$O-Lactose.

* * * * *